United States Patent [19]

Bacha et al.

[11] 4,065,470

[45] Dec. 27, 1977

[54] PROCESS FOR PRODUCING MALEIC ANHYDRIDE FROM MIXTURE OF FIVE AND SIX CARBON HYDROCARBONS

[75] Inventors: John D. Bacha, Monroeville; Joseph S. Matthews, Pittsburgh; Charles M. Selwitz, Monroeville, all of Pa.

[73] Assignee: Gulf Research & Development Company, Pittsburgh, Pa.

[21] Appl. No.: 714,047

[22] Filed: Aug. 13, 1976

[51] Int. Cl.$^2$ .......................................... C07D 307/60
[52] U.S. Cl. .............................................. 260/346.75
[58] Field of Search .................................. 260/346.8 A

[56] References Cited

U.S. PATENT DOCUMENTS 2,079,490  5/1937  Conover ............................. 260/533

OTHER PUBLICATIONS

Yamamoto et al., Sekiyu Gakkai Shi, 1972, vol. 15(11), pp. 932-935 (Chem. Abst. vol. 78 (1973) 71523u).
Yamazaki et al., Chem. Abst. vol. 82 (1975) 171664s.
Ikawa et al., Chem. Abst. (1974) vol. 81, 64278b.

*Primary Examiner*—Henry R. Jiles
*Assistant Examiner*—Bernard Dentz

[57] ABSTRACT

A process for producing maleic anhydride from a hydrocarbon mixture containing $C_5$ monoolefinic hydrocarbons, $C_5$ diolefinic hydrocarbons, (cyclic and acylic) $C_5$ paraffins, $C_6$ paraffins and benzene which involves separating the $C_5$ cyclic diolefinic hydrocarbons from the mixture and then reacting the resulting mixture with molecular oxygen in vapor phase in the presence of an oxidation catalyst at elevated temperatures.

9 Claims, No Drawings

PROCESS FOR PRODUCING MALEIC ANHYDRIDE FROM MIXTURE OF FIVE AND SIX CARBON HYDROCARBONS

BACKGROUND OF THE INVENTION

1. Field of the Invention

This invention relates to a process for preparing maleic anhydride from a hydrocarbon mixture containing $C^5$ monoolefinic hydrocarbons, $C_5$ diolefinic hydrocarbons (cyclic and acyclic), $C_5$ paraffins, $C_6$ paraffins and benzene wherein the $C_5$ cyclic diolefinic hydrocarbons have been removed and the resulting mixture in vapor phase is reacted with molecular oxygen in the presence of an oxidation catalyst at elevated temperatures.

2. Description of the Prior Art

The catalytic oxidation of hydrocarbons. alone or mixtures thereof, to produce a product containing maleic anhydride is known. Included among the hydrocarbon charge stocks are aromatic hydrocarbons, such as benzene, toluene, ortho-xylene etc.; monoolefinic hydrocarbons such as butene-1, butene-2, etc.; diolefinic hydrocarbons, such as 2,3-dimethyl butadiene, 1,3-butadiene, isoprene, 1,3-pentadiene, etc. This is shown, for example, in U.S. Pat. Nos. 3,156,705 to Kerr 3,288,721 to Kerr and 3,538,122 to Friedrichsen et al. In some cases these charges have been obtained from cracked naphthas, as, for example, in U.S. Pat. Nos. 2,719,853 and 2,773,838 to Reid et al.

Naphtha is a volatile liquid hydrocarbon mixture produced by the fractional distillation of petroleum with a boiling range at from about 27° to about 260° C. comprising acylic and cyclic paraffins and olefins and aromatic hydrocarbons. A significant amount of light olefins, for example, ethylene and propylene, are obtained by way of steam cracking of naphtha employing fired tubular furnaces operating at short residence time, high temperature and low hydrocarbon partial pressure. In addition to the light olefins, hydrogen, methane, ethane, propane, $C_4$ paraffins, olefins and diolefins and a host of higher (normally liquid) hydrocarbons are also produced. In processing the product, water (from steam) is separated from the hydrocarbon mixture, then light (normally gaseous $C_1-C_4$) hydrocarbons are separated from heavier (normally liquid $C_5+$) hydrocarbons and finally the mixtures are processed to separate and purify desired product (s).

Of the light hydrocarbons, ethylene and propylene are most desirable and are therefore purified for sale as chemical feedstocks. Hydrogen and methane are used for fuel, while ethane and propane are recycled to the naphtha cracker. The butadiene and butylene in the $C_4$ fraction are separated and sold as chemicals or as synthetic rubber feedstocks. The remaining $C_4$ paraffins are used as fuel or recycled to the naphtha cracker.

The liquid hydrocarbon product consists essentially of a mixture of $C_5$ through $C_9$ hydrocarbons having a boiling point at atmospheric pressure of about 24° to about 204° C. Normally, the liquid hydrocarbon product is separated into $C_5$ hydrocarbons, $C_6-C_8$ hydrocarbons $C_9+$ hydrocarbons. The $C_6-C_8$ hydrocarbons therein are mainly aromatics, for example, benzene, toluene, xylenes, etc., commonly referred to as "BTX components".

The mixture of $C_5$ hydrocarbons contains a significant amount of BTX components and other $C_6$ hydrocarbons, for example, n-hexane. Their presence in the $C_5$ hydrocarbon mixture is due to the fact that in order to minimize the presence of $C_5$'s in the BTX component mixture when the liquid hydrocarbon product is separated some $C_6$'s are taken overhead with the $C_5$'s.

The mixture of $C_5$ hydrocarbons also contains a significant amount, for example, from about 20 to 25 weight per cent of isoprene. Since isoprene is valuable for the synthesis of polyisoprene, isoprene is removed from the $C_5$ mixture. One separation technique involves concentration of the isoprene and then extraction of the same from the concentrate.

The $C_5$ mixture remaining contains primarily $C_5$ monolefinic hydrocarbons, for example, pentene-1, pentene-2, 2-methylbutene-1, 2-methylbutene-2, 3-methylbutene-1, cyclopentene, etc; $C_5$ diolefinic hydrocarbons (cyclic and acyclic), for example, 1,3-pentadiene, 1,4-pentadiene, isoprene, cyclopentadiene, etc.; $C_5$ paraffins, for example, 2-methylbutane, n-pentane, cyclopentane, etc., $C_6$ paraffins, for example, n-hexane, 2-methylpentane, 3-methylpentane, 2,3-dimethylbutane, etc., and benzene.

Such a commercial mixture is defined below in Table I.

TABLE I

| Compound | Weight Per Cent |
|---|---|
| Pentene-1 | <0.1 |
| 2-Methylbutene-1 | <0.1 |
| Isoprene | 0.7 |
| Isopentyne | <0.1 |
| n-Pentane | 0.4 |
| Pentyne-1 | <0.1 |
| Pentyne-2 | 0.5 |
| 2-Methylbutene-2 | 0.7 |
| Cyclopentadiene | 39.7 |
| 1,3-Pentadiene | 7.5 |
| Cyclopentene | 8.2 |
| Cyclopentane | 2.4 |
| n-Hexane | 28.4 |
| Benzene | 10.6 |

Reference is made in the above table to cyclopentadiene, but such terminology herein is also intended to include its dimer dicyclopentadiene, since the two can be in equilibrium with each other, depending on the conditions in which each finds itself.

SUMMARY OF THE INVENTION

We have found that $C_5$ mixtures, such as those defined above, particularly those mixtures obtained as a result of the steam cracking of naphtha from which $C_4$ and lower and $C_6$ and higher components and isoprene have been removed, can be reacted in the vapor phase with oxygen in the presence of an oxidation catalyst to obtain high yields of maleic anhydride, provided the $C_5$ cyclic diolefins are first removed from $C_5$ mixture prior to reaction.

$C_5$ mixtures suitable for use herein will have the composition defined below in Table II.

TABLE II

| | Weight Per Cent | |
|---|---|---|
| Component | Broad Range | Preferred Range |
| $C_5$ Monolefinic Hydrocarbons | 5 to 50 | 10 to 30 |
| $C_5$ Diolefinic Hydrocarbons | 10 to 20 | 0 to 15 |
| $C_5$ Paraffins | 5 to 75 | 20 to 40 |
| $C_6$ Paraffins | 5 to 75 | 20 to 40 |
| Benzene | 5 to 75 | 15 to 50 |

In removing the $C_5$ cyclic diolefinic hydrocarbons for example cyclopentadiene from the $C_5$ mixtures defined in Table II any suitable or conventional procedure can be used. Thus, to remove cyclopentadiene, the mixture can be heated, for example, in a closed system for about ten minutes to about two hours, preferably about 0.2 to about 1.5 hours, at a temperature of about 30° to about 150° C., preferably about 50° to about 120° C., and at a pressure of about 20 to About 200 pounds per square inch gauge (about 1.4 to about 14 kilograms per square centimeter), preferably about 50 to about 150 pounds per square inch gauge (about 3.5 to about 10.5 kilograms per square centimeter). The $C_5$ cyclic diolefinic hydrocarbon will dimerize and the remainder of the mixture is then separated therefrom. Thus, in the case of cyclopentadiene, dicyclopentadiene will be formed, boiling at 170° C. at atmospheric pressure. Distilling this mixture at a temperature of about 100° C. or below at about atmospheric pressure and below will result in the distillation of all the components except dicyclopentadiene.

Production of maleic anhydride using the above $C_5$ mixture can be carried out in the conventional manner for catalytic gas phase reactions. Thus, a mixture of the $C_5$ mixture and molecular oxygen (oxygen or air) is passed over any conventional oxidation catalyst at a space velocity (volume of feed per volume of catalyst per hour) of about 0.01 to about 0.1, preferably about 0.04 to about 0.08, while maintaining a temperature of about 350° to about 500° C., preferably about 400° to about 475° C., and a pressure of about 5 to about 50 pounds per square inch gauge (about 0.35 to about 3.5 kilograms per square centimeter), preferably about 15 to about 20 pounds per square inch gauge (about 1.0 to about 1.4 kilograms per square centimeter) in the reaction zone. The amount of hydrocarbon used will be in the range of about 0.5 to about 1.7, preferably about 1.0 to about 1.4, volume per cent. Recovery of the maleic anhydride from the reaction mixture can be effected in any conventional manner. Thus, the reaction mixture can be cooled to a temperature of about 20° to about 40° C. and then passed to a water scrubber wherein the maleic anhydride is removed from the cooled mixture.

Any conventional oxidation catalyst used in treating mixtures of hydrocarbons and oxygen in vapor phase at elevated temperatures to obtain maleic anhydride can be employed herein. Examples of such catalysts are vanadium phosphates, vanadium nickel phosphates, vanadium zinc phosphates, basic vanadium titanium molybdates, etc. A particularly suitable catalyst for use herein is a vanadium phosphate containing vanadium, phosphorus and oxygen defined by the following arrangement: $V_2O_5/P_2O_5$, wherein the atomic ratio of vanadium to phosphorus is in the range of about 3:5 to about 5:4, preferably about 3.5:5 to about 4.5:4. The catalyst can be placed, if desired, on any suitable carrier, for example, glass beads, ceramic beads, carborundum chips, stainless steel shot, etc.

DESCRIPTION OF PREFERRED EMBODIMENTS

EXAMPLE I

Two blends were prepared, identical in composition, except that one contained cyclopentadiene and the other did not. The blends are identified below in Table III.

TABLE III

| Component | Weight Per Cent | |
|---|---|---|
| | Blend A | Blend B |
| Cyclopentadiene | 40.5 | None |
| 1,3-Pentadiene | 7.8 | 13.1 |
| Cyclopentene | 8.5 | 14.4 |
| Cyclopentane | 2.5 | 4.2 |
| n-Hexane | 29.6 | 49.7 |
| Benzene | 11.0 | 18.6 |

Each of these blends was passed in admixture with about 1.1 volume percent of hydrocarbon in air over a vanadium phosphate catalyst at a space velocity of 0.06, a temperature of 450° C. and atmospheric pressure over a 2-hour period. The catalyst can be defined as follows: $V_2O_5/P_2O_5$, wherein the atomic ratio of vanadium to phosphorus is 4:5. The results obtained are summarized below in Table IV.

TABLE IV

| Feedstock | Grams of Feedstock | Grams of Maleic Anhydride Produced | Pounds of Maleic Anhydride Produced Per Pound of Feedstock |
|---|---|---|---|
| A | 9.0 | 5.3 | 0.59 |
| B | 7.7 | 5.8 | 0.75 |

The above data show the criticality of removing $C_5$ cyclic diolefinic hydrocarbon from the $C_5$ charge mixture prior to reaction. Note that when Blend B, with no $C_5$ cyclic diolefinic hydrocarbon present, was used, the pounds of maleic anhydride obtained per pound of feedstock was 27 percent higher than when the otherwise identical Blend A was used but which also contained dicyclopentadiene.

Obviously, many modifications and variations of the invention, as hereinabove set forth, can be made without departing from the spirit and scope thereof, and therefore only such limitations should be imposed as are indicated in the appended claims.

We claim:

1. A process for preparing maleic anhydride from a hydrocarbon mixture containing $C_5$ monoolefinic hydrocarbons, $C_5$ cyclic and acyclic diolefinic hydrocarbons, $C_5$ paraffins, $C_6$ paraffins and benzene which comprises separating $C_5$ cyclic diolefinic hydrocarbons from said hydrocarbon mixture and then reacting the resulting mixture with molecular oxygen in the presence of an oxidation catalyst.

2. The process of claim 1 wherein said hydrocarbon mixture contains the following components in the following amounts.

| Component | Weight Per Cent |
|---|---|
| $C_5$ Monolefinic Hydrocarbons | 5 to 50 |
| $C_5$ Diolefinic Hydrocarbons | 10 to 20 |
| $C_5$ Paraffins | 5 to 75 |
| $C_6$ Paraffins | 5 to 75 |
| Benzene | 5 to 75 |

3. The process of claim 1 wherein said hydrocarbon mixture contains cyclopentadiene, 1,3-pentadiene, cyclopentene, cyclopentane, n-hexane and benzene.

4. The process of claim 1 wherein said $C_5$ cyclic diolefin is cyclopentadiene.

5. The process of claim 1 wherein said oxidation catalyst is a vanadium phosphate catalyst defined by $V_2O_5/P_2O_5$ wherein the atomic ratio of vanadium to phosphorus is about 3:5 to about 5:4.

6. The process of claim 1 wherein said oxidation catalyst is a vanadium phosphate catalyst defined by $V_2O_5/P_2O_5$ wherein the atomic ratio of vanadium to phosphorus is about 3.5:5 to about 4.5:4.

7. The process of claim 1 wherein said reaction is carried out at a temperature of about 350° to about 500° C.

8. The process of claim 1 wherein said reaction is carried out at a temperature of about 400° to about 475° C.

9. The process of claim 1 wherein said hydrocarbon mixture has been obtained from a cracked naphtha from which $C_4$ and lower and $C_6$ and higher components and isoprene have been removed.

* * * * *